United States Patent [19]

Takamatsu

[11] Patent Number: 4,487,489
[45] Date of Patent: Dec. 11, 1984

[54] ENDOSCOPIC PHOTOGRAPHING APPARATUS

[75] Inventor: Takeshi Takamatsu, Tokyo, Japan

[73] Assignee: Olympus Optical Co., Ltd., Tokyo, Japan

[21] Appl. No.: 336,843

[22] Filed: Jan. 4, 1982

[30] Foreign Application Priority Data

Jan. 14, 1981 [JP] Japan .................................. 56-4288

[51] Int. Cl.³ ...................... G03B 29/00; A61B 1/04; A61B 17/36
[52] U.S. Cl. ........................................ 354/62; 128/6; 128/303.15
[58] Field of Search ......................... 354/62; 128/3-9, 128/303.14, 303.15

[56] References Cited

U.S. PATENT DOCUMENTS

| 2,280,561 | 4/1942 | Wappler | 354/62 |
| 3,903,892 | 9/1975 | Komiya | 128/303.15 |
| 3,923,063 | 12/1975 | Andrews et al. | 128/303.14 |
| 3,952,748 | 4/1976 | Kaliher et al. | 128/303.14 |
| 4,094,320 | 6/1978 | Newton et al. | 128/303.14 |
| 4,153,356 | 5/1979 | Hama | 354/62 |
| 4,343,300 | 8/1982 | Hattori | 354/62 X |
| 4,374,517 | 2/1983 | Hagiwara | 128/6 |

FOREIGN PATENT DOCUMENTS 2043278 10/1980 United Kingdom .

OTHER PUBLICATIONS

European pat. appln. A-0 018 126, (Olympus Optical Co.), Abstract; p. 11, line 35 to p. 12, line 12; FIGS. 1-3.

Primary Examiner—William B. Perkey

[57] ABSTRACT

An endoscope and an electrosurgical device are assembled such that when endoscopic operation is started during electrosurgical operation conducted with the output of the electrosurgical device, the output of the electrosurgical device is interrupted until the photographing is ended.

6 Claims, 4 Drawing Figures

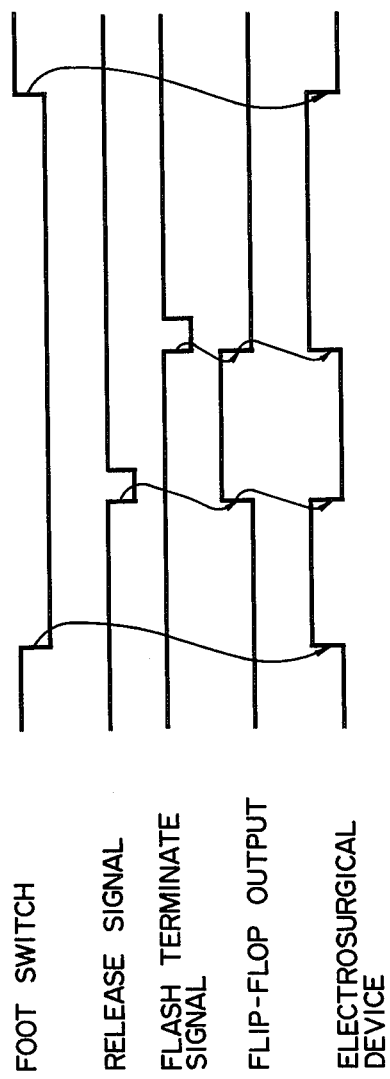

4,487,489

ENDOSCOPIC PHOTOGRAPHING APPARATUS

BACKGROUND OF THE INVENTION

This invention relates to endoscopic photographing apparatus and, more particularly, endoscopic photographing apparatus used with medical electronic apparatus.

Recently, it has been in practice to carry out endoscopic treatment of the body by using an endoscope in combination with a medical electronic device such as electric bistoury device. However, when endoscopic photographing is made during the operation of the electric bistoury device, noise generated from the electric bistoury device is introduced into a release signal or light measurement signal to have adverse effects upon the photographing operation and cause defective exposure.

SUMMARY OF THE INVENTION

An object of the invention, accordingly, is to provide an endoscopic photographing apparatus, with which the photographing operation is not influenced by any noise component generated from a medical electronic device.

According to the invention, there is provided an endoscopic photographing apparatus, which comprises an endoscope, a camera mounted on an eyepiece section of the endoscope, and a light supply unit for generating observation light and photographing light, and which is provided with means for detecting the start of the photographing operation and interrupting the output of a medical electronic device at least until the end of the photographing operation in response to a detection signal obtained by the detection.

BRIEF DESCRIPTION OF THE DRAWINGS

FIG. 4 is a time chart for illustrating the operation of the endoscopic photographing apparatus shown in FIG. 3.

DETAILED DESCRIPTION OF THE PREFERRED EMBODIMENT

Figure 1:
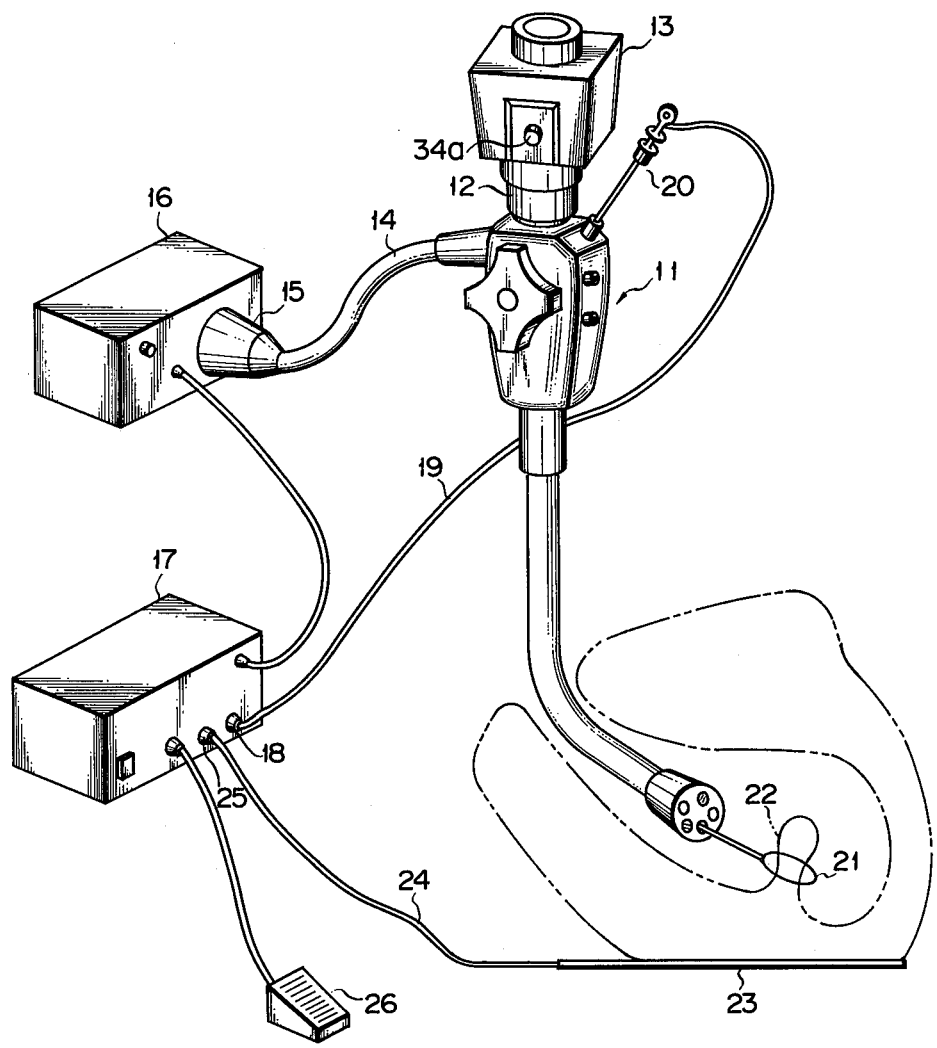
FIG. 1 is a perspective view showing one embodiment of the endoscopic photographing apparatus according to the invention.
Figure 2:
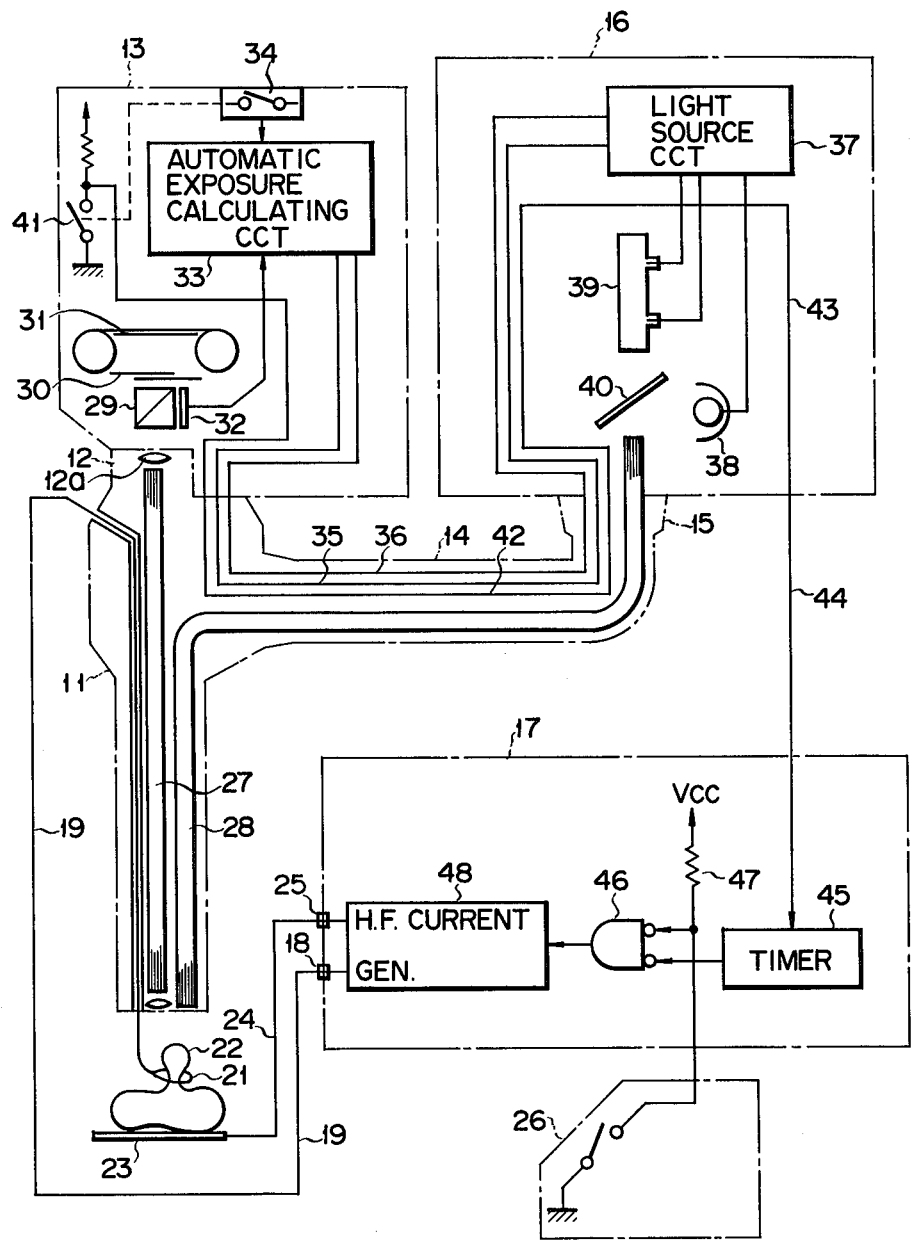
FIG. 2 is a circuit diagram showing the electric circuit of the endoscopic photographing apparatus shown in FIG. 1.

Referring to FIGS. 1 and 2, a camera 13 is mounted on an eyepiece section 12 of an endoscope 11, and a connector 15 at the end of a universal cord 14 is connected to a light supply unit 16. An electrosurgical device (electric bistoury device) 17 has an active electrode terminal 18 which is connected through a cord 19 to an electrosurgical instrument 20. The electrosurgical instrument 20 is inserted through a forceps channel of the endoscope 11 and is provided at the tip with an active electrode 21 for clamping the tissue 22. A patient electrode 23 is connected through a cord 24 to a patient electrode terminal 25. A foot switch 26 is connected to the electrosurgical device 17 for on-off controlling the electrosurgical device 17.

As shown in FIG. 2, the endoscope 11 is provided with an image guide 27 and a light guide 28. In the camera 13, a beam splitter 29, a shutter 30 and a film 31 are provided in the mentioned order to face an eyepiece lens 12a of the eyepiece section 12 of the endoscope 11. A light receiving element (photodiode) 32 is provided on one side of the beam splitter 29. The photodiode 32 is connected to an automatic exposure calculating circuit 33. The automatic exposure calculating circuit 33 is a usual exposure calculating circuit for calculating exposure according to the output of the photodiode 32 in response to the closure of a release switch 34. The automatic exposure calculating circuit 33 has a release signal output terminal and a flash terminate signal output terminal. These terminals are connected through respective transmission lines 35 and 36 of the endoscope 11 to a light source circuit 37 of the light supply unit 16. The light source circuit 37 is connected to an observation light source (e.g. halogen lamp) 38 and a photographing light source (e.g. electronic flash lamp) 39 for on-off controlling these lamps. The light paths of the lamps 38 and 39 with respect to the light guide 28 are switched by a usual switching system using a light path switching mirror 40. The camera 13 is provided with a switch 41 which is interlocked to the release switch 34. The switch 41 is connected through the transmission line 42 of the endoscope 11, signal line 43 of the light supply unit 16 and cord 44 to an interval timer 45 of the electrosurgical device 17. The output terminal of the timer 45 is connected to one of the input terminals of a NOR gate 46. The other input terminal of the NOR gate 46 is connected through a resistor 47 to a power supply Vcc and is also connected to a foot switch 26. The output terminal of the NOR gate 46 is connected to a trigger input terminal of a high frequency current generator 48.

In the above construction, when the switch 41 and foot switch 26 are "off", the output of the timer 45 is at an L (low) level, and thus the input terminals of the NOR gate 46 are respectively at H (high) and L levels so that the output of the NOR gate 46 is at L level. When the output of the NOR gate 46 is at the L level, the high frequency current generator 48 is inoperative. When the foot switch 26 is closed in this state, both the input terminals of the NOR gate 46 come up with the L level, so that the NOR gate 46 provides an H level signal. With the appearance of the H level signal from the NOR gate 46, the high frequency current generator 48 is triggered to provide high frequency current. This high frequency current is led through the cords 19 and 24 to the active electrode 21 and patient electrode 23 to burn the patient's tissue 22. When the release button 34a (FIG. 1) is depressed during this burning treatment for taking a picture of the patient's tissue 22, the release switch 34 and interlock switch 41 are closed. As a result, the automatic exposure calculating circuit 33 generates a release signal, which is fed through the transmission line 35 to the light source circuit 37. Also, the switch 41 provides an interrupt signal which is fed through the transmission line 42, signal line 43 and cord 44 to the timer 45 of the electro-surgical device 17. In response to the interrupt signal, the timer 45 supplies an H level signal to the NOR gate 46. As a result, the output of the NOR gate 46 goes to the L level, whereupon the generation of the high frequency current from the high frequency current generator 48 is stopped. At this time, the light source circuit 37 starts a photographing operation in response to the release signal. In the photographing operation, the shutter 30 of the camera 13 is released and the light path switching mirror 40 is turned upright. The flash tube 39 is caused to emit flashlight at an instant when the shutter 30 is fully released. The flashlight from the flash tube 39 is transmitted through the light guide 28 to the patient's tissue 22 to illuminate the tissue. When the reflected light from the tissue is incident through the image guide 27 to the beam splitter 32, the photodiode 32 generates a photoelectric output corresponding to the reflected light received. With the photoelectric output supplied to the automatic exposure calculating circuit 33, the exposure period calculation is started. When a proper exposure period is obtained, the automatic exposure calculating circuit 33 generates a flash terminate signal. This flash terminate signal is transmitted through the transmission line 36 to the light source circuit 37. The light source circuit 37 stops the flashlight emission of the flash tube 39 in response to the flash terminate signal. Subsequently, the camera shutter 30 is closed, and the light path switching mirror 40 is restored to the initial position. Also, the release switch 34 and switch 41 are both opened at this time. This brings an end to one cycle of the photographing operation. The timer 45 of the electrosurgical device 17 provides the H level signal for a period required for the aforementioned one cycle of photographing operation. The timer 45 of the electrosurgical device 17 provides the H level signal for a period required for the aforementioned one cycle of photographing operation, for instance 250 msec., and changes the output to the L level at the instant of the end of the photographing operation. When the output of the timer 45 is changed to the L level, the high frequency current generator 48 again produces the high frequency current to resume the burning treatment. When the foot switch 26 is opened after the end of the burning treatment of the patient's tissue 22, the output of the NOR gate 46 is changed to the L level, whereupon the high frequency current generator 48 stops the generation of high frequency current.

It is to be understood that when the photographing operation is started while the patient's tissue is being treated by the electrosurgical device, i.e., while the high frequency current is being generated, the generation of the high frequency current is interrupted only during the photographing operation, so that it is possible to obtain proper photographing without the photographing signal such as the release signal being influenced by any noise component of high frequency current. The period of interruption of the electrosurgical device is about 250 msec., i.e., about 0.25 sec., which is considerably short compared to one output cycle period of the electrosurgical device, i.e., about 5 sec., so that the aforementioned interruption of the electrosurgical operation has no substantial adverse effect upon the operation.

The switch 41 in the above embodiment may be served by the release switch 34 as well, or it may be served by an X contact of the camera 13, an FP contact or other synchro-contacts. Further, the switch 41 may be replaced with a flash start signal from the light source circuit 37. Further, the timer 45, NOR gate 46 and resistor 47 may be provided in the foot switch 26 or light supply circuit 16. Further, as the signal for interrupting the operation of the electrosurgical device a light signal or a supersonic signal may be used, and as the signal line an optical fiber or a supersonic wave guide medium may be used.

Figure 3:
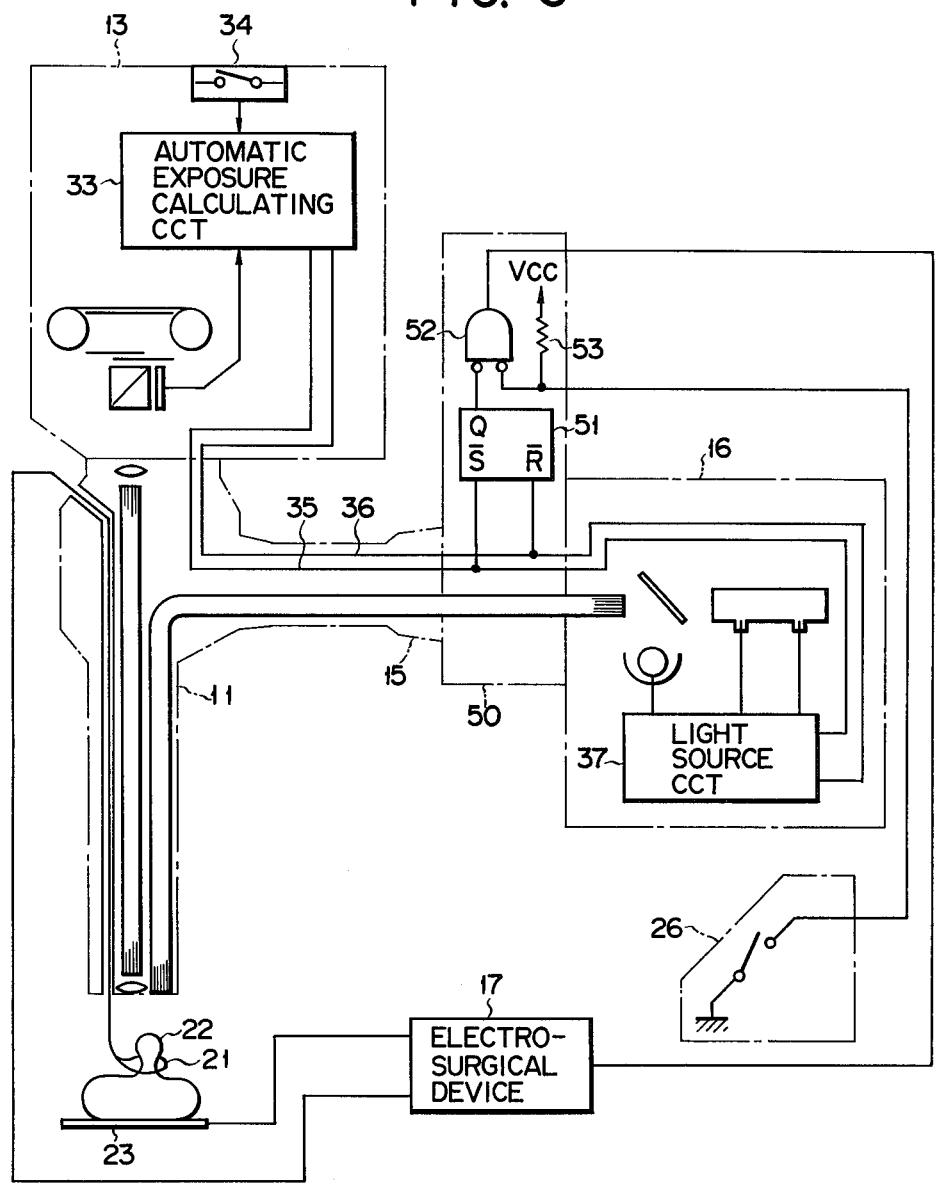
FIG. 3 is a circuit diagram showing the electric circuit of a different embodiment of the endoscopic photographing apparatus according to the invention.

Now, a different embodiment will be described with reference to FIG. 3. In this embodiment, an adapter 50 is mounted between connector 15 and light supply circuit 16. The adapter 50 includes a flip-flop 51, with the set terminal $\overline{S}$ thereof connected to release signal transmission line 35 and the reset terminal $\overline{R}$ connected to flash terminate signal transmission line 36. The output terminal Q of the flip-flop 51 is connected to a first input terminal of a NOR gate 52. A second input terminal of the NOR gate 52 is connected to the foot switch 26 and is also connected through a resistor 53 to a power supply Vcc.

In this embodiment, while the electrosurgical device 17 is in operation caused with the closure of the foot switch 26, but the first and second input terminals of the NOR gate 52 are held at the L level, and the output of the NOR gate 52 is at the H level. When the release switch 34 is closed in this state, the automatic exposure calculating circuit 33 and light source circuit 37 are rendered operative, whereby an L level pulse signal is transmitted through the release signal transmission line 35 to the light source circuit 37 to render the photographing light source operative. The pulse signal is also supplied to the set terminal $\overline{S}$ of the flip-flop 51, and the output of the flip-flop 51 is changed to the H level as shown in the time chart of FIG. 4. In response to this H level signal the output of the NOR gate 52 is changed to the L level, whereupon the operation of the electrosurgical device 17 is stopped. When the exposure in the photographing operation is completed, the L level pulse signal, i.e., flash terminate signal, is transmitted through the signal line 36 to the light source circuit 37, and it is also supplied to the reset terminal $\overline{R}$ of the flip-flop 51. As a result, the output of the flip-flop 51 is changed to the L level to change the output of the NOR gate 52 to the L level. Thus, the electrosurgical device 17 is driven again.

With the above embodiment, which incorporates the adapter 50, the aim of the invention can be achieved without modifying the endoscope, camera, light source unit or foot switch. The adapter may be provided in the camera, light source unit or endoscope. Further, the release signal and flash terminate signal may be replaced with a multiplex signal, or the signal lines may be replaced with a common line. Further, it is possible to transmit an encoded signal.

As has been described in the foregoing, according to the invention the operation of the electrosurgical operation is interrupted at least during the period of the photographing operation, so that satisfactory photographing can be obtained without the photographing signal being influenced by any noise component generated from the electrosurgical device. Further, where a single lens reflex is used as the camera, the endoscopic observation is impossible during photographing, but since the electrosurgical device is held inoperative during this photographing period, the photographing can be safely carried out even though the endoscopic observation cannot be made.

While the above embodiment have concerned with electrosurgical devices, the invention is also applicable to other medical electronic devices where noise component is generated such as laser surgical devices and supersonic devices.

What is claimed is:

1. An endoscopic photographing apparatus comprising:
   an endoscope having an eyepiece section;
   a camera mounted on the eyepiece section of the endoscope;

a light supply unit for emitting light for illuminating a foreground subject through said endoscope;

a medical electronic device connected to said endoscope for generating a high frequency current causing consequential noise components during operation of same for medical purposes;

means for detecting the start of a photographing operation period of said camera to produce an output; and and means for stopping the generation of output of the high frequency current of said medical electronic device at least for the period of the photographing operation in response to the detection of the start of the photographing operation.

2. The endoscopic photographing apparatus according to claim 1, wherein said output generation stopping means includes a timer for holding said medical electronic device inoperative for said photographing operation period in response to the output of said detecting means.

3. The endoscopic photographing apparatus according to claim 1, wherein said camera includes an automatic exposure calculating circuit for generating a release signal in response to a release operation and generating an exposure terminal signal when a proper exposure is obtained, said detecting means including an electronic circuit set in response to said release signal and reset in response to said exposure signal, and said stopping means including means for stopping the operation of said medical electronic device in response to a set signal of said electronic circuit and causing the resumption of the operation of said medical electronic device in response to a reset signal of said electronic circuit.

4. The endoscopic photographing apparatus according to any of claims 1, 2 or 3, wherein said detecting means and output stopping means are provided in said medical electronic device.

5. The endoscopic photographing apparatus according to any of claims 1, 2 or 3, wherein said medical electronic device is an electrosurgical device.

6. The endoscopic photographing apparatus according to any of claims 1, 2 or 3, wherein said detecting means and output stopping means are assembled in an adapter, said adapter being mounted between a connector of the endoscope and the light supply unit.

* * * * *